United States Patent [19]

Morifuji

[11] Patent Number: 4,886,494

[45] Date of Patent: Dec. 12, 1989

[54] MILKING APPARATUS

[76] Inventor: Yasuo Morifuji, Maison de Colline 106, 7-17, Asahigaoka 1-chome, Ikedashi, Osaka, Japan

[21] Appl. No.: 179,936

[22] Filed: Apr. 11, 1988

[30] Foreign Application Priority Data

Apr. 9, 1987 [JP] Japan .................................. 62-88524
Dec. 28, 1987 [JP] Japan ................................. 62-335105

[51] Int. Cl.$^4$ .............................................. A61M 1/06
[52] U.S. Cl. .................................... 604/74; 604/347
[58] Field of Search ................................... 604/73–75, 604/347; 119/14.34, 14.43, 14.46; 251/321; 137/205

[56] References Cited

U.S. PATENT DOCUMENTS 4,673,388 7/1987 Schlensog et al. ..................... 604/74
4,803,950 2/1989 Griffin et al. ..................... 119/14.55

FOREIGN PATENT DOCUMENTS 2127293 4/1984 United Kingdom .................. 604/74

*Primary Examiner*—Jerome L. Kruter

[57] ABSTRACT

A milking apparatus includes a bottle for storing drawn mother's milk, a milking section to be pressed against the mother's breast, and a suction portion including a suction generating section, for generating a suction in the bottle, and a pressure adjusting mechanism for adjusting the amount of suction. The pressure adjusting mechanism and the suction generating section include an attaching body formed with an open-air introducing hole, a compression coil spring, a valve rod having a tapered surface, a diaphragm having a valve seat adapted to closely contact with the tapered surface, a cap cooperating with said diaphragm to define a suction chamber therebetween, a pressure releasing push button having a cam surface and adapted to arrest the valve rod, and a pressure adjusting knob for applying a pressing force to the cam surface of said push button. Further, the milking apparatus includes a dome-shaped cup with a collar interposed between the bottle and the milking portion with its vertex facing downward. The collar is provided with a plurality of suction holes for communication between the bottle and milking portion, and a through hole is formed in the vertex A non-return valve which is normally open is disposed at the communicating portion betwen the bottle and milking protion.

10 Claims, 11 Drawing Sheets

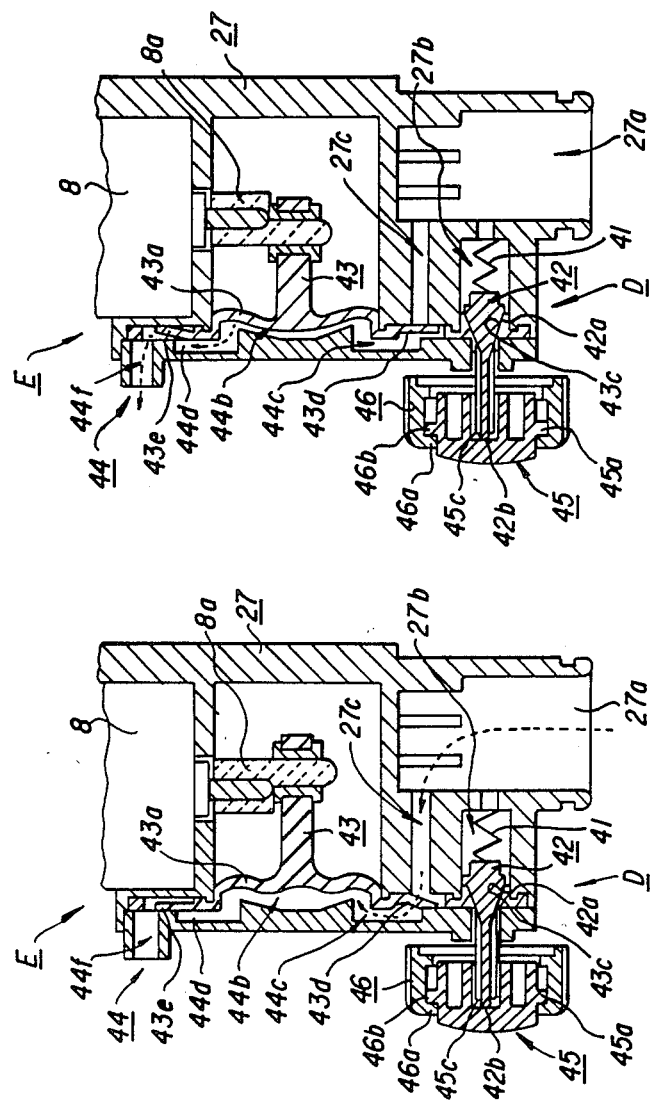

MILKING APPARATUS

BACKGROUND OF THE INVENTION

The present invention relates to a milking apparatus for drawing a mother's milk into a container or bottle. More specifically, the present invention relates to a pressure adjusting mechanism for adjusting a suction created in the container used for storing the mother's milk. Also, the present invention specifically relates to a milking apparatus which prevents the counter flow of milk from the container when tipped or turned over, and also prevents clogging of the device with milk.

Milking apparatuses having an electrically powered suction device for drawing mother's milk are becoming increasingly popular to use. However, such milking apparatuses do not have improved suction action and thus tend to draw the mother's milk one-sidedly, overloading the breast, thus having a drawback of causing discomfort for the mother.

The applicant has already proposed, in Japanese Utility Model Application No. 141247/1984 (Japanese Utility Model Application Laid-Open Specification No. 54844/1986), a milker designed so that its suction pressure can be finely adjusted. This milker will now be described with reference to FIGS. 14 through 22. FIG. 14 is a complete perspective view of a milker and FIG. 15 is a fragmentary, enlarged vertical sectional view.

The milker comprises a bottle A for storing drawn mother's milk, a milking section B to be pressed against the mother's breast, and an electrically powered suction portion C for creating a suction or negative pressure in bottle these components being vertically connected together, so that the milking section B is interposed between the bottle A and the suction portion C in a linear fashion.

The milking section comprises a substantially cylindrical base portion 1, a barrel portion 2 extending generally horizontally from and integral with the upper portion of base portion 1. A funnel-shaped cup portion 3 spreads from the front end of barrel 2. The lower portion of the base portion 1 of milking section B terminates in a lower connecting portion 1a adapted to be threadedly engaged with the upper portion of bottle A. Further, the upper portion of base portion 1 terminates in an upper connecting portion 1b adapted to receive the lower portion of electrically powered suction portion C. Further, the junction between the barrel portion 2 of the milking section B and the cup portion 3 has a removable adapter 4 for reducing the diameter of the barrel portion 2. The adapter 4 is designed to closely contact the areola mammae of the mother's breast to increase the suction force or to compensate for small nipples, nipple depression or flat nipples.

The electrically powered suction portion C comprises a main body 5 fitted in the upper connecting portion 1b, an upper lid 6 fitted on the upper portion of main body 5, and an attaching body 7 disposed in the main body 5. Motor 8 and battery 9 which are electrically connected together by a wire (not shown) and are positioned on attaching body 7. The motor 8 has a crank pin 8a mounted thereon and the battery 9 can be replaced by removing the upper lid 9 from the main body 5. The main body 5 is in the form of two cases 5a and 5b which are vertically split. In FIG. 15, the left-hand case 5a is centrally formed with a vertical hole which holds a slidable switch 10 fixed in position by a screw 10a from the inside. A portion of the main body 5 is located below the switch 10 and adjacent the upper connecting portion 1b of the milking section B is formed with a horizontal hole 5c in which the pressure adjusting mechanism D is installed.

An exploded vertical sectional front view of the pressure adjusting mechanism D is shown in FIG. 16 and the same will now be described. In this figure, the left-hand side will be referred to as the outer side and the right-hand side as the inner side. The pressure adjusting mechanism D is formed with an open-air introducing hole 7a below the attaching body 7 and coaxial with horizontal hole 5c. Eight parts are fitted in said open-air introducing hole 7a: a compression coil spring a valve rod 12, packing 13, a valve seat 14, a pressure releasing button shaft portion 15, a pressure adjusting screw 16, a pressure adjusting knob 17 and a pressure releasing push button 18, in order from the inner side. The open-air introducing hole 7a is internally threaded at 7b. The valve seat 14 and the outer periphery of the inner side of the pressure adjusting screw 16 are externally threaded at 14a and 16a, respectively. The external threads 14a and 16a of valve seat 14 and pressure adjusting screw 16 are fitted to the internal thread 7b of the open-air introducing hole 7a. The valve rod 12 and packing 13 are fitted together and positioned in the open-air introducing hole 7a. Thereupon, the compression coil spring 11 urges the valve rod 12 outward to cause packing 13 to closely contact valve seat 14.

A sectional view of the pressure adjusting screw 16 taken along the line X—X is shown in FIG. 17, and a sectional view of the pressure adjusting knob 17 taken along the line Y—Y is shown in FIG. 18. As shown in the two figures, the pressure adjusting screw 16 and pressure adjusting knob 17 are formed with splines 16b and 17a (which are referred to as knurling in Japanese Utility Model Application Laid-Open Specification No. 54844/1986) and are thereby fitted and joined together. FIG. 19 is a sectional view showing them in this fitted and joined state and also showing the pressure releasing button shaft portion 15. In this figure, the reference numeral 5d denotes a stopper projecting from the case 5a at the upper edge of the horizontal hole 5c. The pressure adjusting knob 17 is internally formed with a locking piece 17b adapted to be arrested by the stopper 5d, whereby the angle of rotation of the pressure adjusting knob 17 is controlled so that it is within approximately 360 degrees.

The attaching body 7 of the pressure adjusting mechanism D has a suction or negative pressure generating section attached thereto, and an exploded sectional view of it is shown in FIG. 16. The suction or negative pressure generating section E comprises the attaching body 7, diaphragm 19 and cap 20. A right-hand side view of the attaching body 7 is shown in FIG. 20, a left-hand side view of the diaphragm 19 is shown in FIG. 21 and a left-hand side view of the cap 20 is shown in FIG. 22. The diaphragm 19 comprises a vibrating portion 19b outwardly projecting to form a suction chamber 19a, a suction valve 19c and an exhaust chamber 19d which are 90 degrees apart from each other. As bushing portion 19a extends outward from the vibrating portion 19b to fit on crank pin 8a. The suction valve 19c opens only inward, while the exhaust valve 19d opens only outward. The attaching body 7 is formed with a fitting hole 7c corresponding to the vibrating portion 19b, and a suction hole 7d and an exhaust hole 7e are formed at positions corresponding with the suction and exhaust valves 19c and 19d. Cap 20 is formed with a projection 20a corresponding to the recess 19a of the diaphragm and has a diameter smaller than the inner diameter of recess 19a. Cap 20 has first and second narrow grooves 20b and 20c corresponding to the suction and exhaust valves 7d and 7e.

The open-air introducing hole 7a and suction hole 7d of the attaching body 7 communicate with the lower end of suction portion C through the air suction hole 7f. However, air suction hole 7f has a filter 21 fitted therein to prevent the milk from flowing back into suction portion C.

In FIG. 15, the lower end 5e of the main body 5 of suction portion C has a fitting ring 22 fitted thereon to elastically press the upper connecting portion 1b of the milking section B for a removable connection. Further, the lower side of the upper connecting portion 1b of milking section B is formed with a small hole 1c for and a guide ring 1d surrounds small hole 1c. The guide ring 1d prevents the milk from being drawn directly into small hole 1c. An annular packing 23 is installed between the lower connecting portion 1a of the milking section B and the bottle A to ensure close contact between the two parts A and B.

The operation of the above-described milker having fine adjustment of the suction pressure will now be set forth.

First, the cup portion 3 of the sucking section B is applied closely to the mother's breast and switch 10 is activated to turn the power on. Then, the crank pin 8a mounted on the motor 8 is eccentrically rotated, and diaphragm 19 engaged with the crank pin 8a is vibrated so that the air in the bottle A is drawn from the small hole 1c of the milking section through filter 21 to the air suction hole 7f of the sucking section C. Thus, a negative pressure is created in bottle A. Therefore, the mother's milk is drawn by the milking section B to flow along the barrel portion 2 of the milking section B and along the guide ring 22 into bottle A where it is collected.

In this case, if the pressure adjusting knob 17, engaged with the pressure adjusting screw 16, is turned counterclockwise, packing 13 engaged with valve rod 12 is moved away from the valve seat 14, allowing open air to flow from the horizontal hole 5c into the air suction hole 7f. Therefore, the suction pressure in bottle A decreases and accordingly so does the milking force or suction force, thus, resulting in gentle milking. Conversely, if the pressure adjusting knob 17 engaged with the pressure adjusting screw 16 is turned clockwise, the packing 13 engaged with the pressure adjusting screw 16 is pressed against the valve seat 14 so that open air will not flow into the air suction hole 7f. Therefore, the greatest negative pressure is created in bottle A so that the milk is strongly drawn by the milking section B. In this manner, by adjusting the degree to which the pressure adjusting knob 17 is turned, the suction force can be accurately varied.

Further, even if the packing 13, engaged with the valve rod 12, is pressed against the valve seat 14, the packing 13 engaged with the valve rod 12 and the valve seat 14 can be instantaneously separated from each other by simply pushing the pressure release push button 18. By pressing the pressure release push button 18, the open air is admitted into the air suction hole 7f through the horizontal hole 5c to reduce the suction pressure. Therefore, by intermittently pressing the pressure release push button 18, the mother's nipple can receive a suitable stimulus, similar to the suckling action of a baby, in order to enable an effective milking procedure.

Moreover, since the pressure adjusting knob 17 and the pressure release button push button 18 are installed on the lower lateral surface of the suction portion C, adjustment of the suction pressure can be made by one hand, while the mother's other hand may be free to be used to massage the periphery of her breast or to help in milking.

The pressure adjusting mechanism D, described above, is composed of a total of 11 parts, including the attaching body 7 and the negative pressure creating section E in order to make it possible to provide for accurately adjustable suction pressure. The manufacture and assembly of such a large number of parts is time consuming and expensive. Thus, a disadvantage of the above-described milker is that it is expensive and time consuming to produce.

Another disadvantage of the above-described milker is that the small hole 1c can often become clogged up. Specifically, if the suction force of the milker is too strong, the mother's milk becomes atomized as it is drawn out, and travels around guide ring 1d and coagulates at small hole 1c in the milking portion B. thus, when the small hole 1c is clogged up, even when the suction portion remains on, the milking process will deteriorate and stop.

A further disadvantage of the above described milker is that when the bottle A is turned sideways, or is tipped over, the mother's milk collected in the bottle will flow into air suction hole 7f from small hole 1c by way of filter 21. Then, the milk flows into the motor mechanism and causes faults in the operation of the motor. This disadvantage occurs often, because milking is often performed in the bedroom, and the milking apparatus is likely to be placed on an unstable surface such as a mattress. Such an unstable surface often results in the milking apparatus being tipped over, causing the milk to contaminate the motor mechanism.

SUMMARY OF THE INVENTION

The instant invention is provided to overcome the disadvantages described above. According to one aspect of the instant invention, the number of parts of the pressure adjusting mechanism has been reduced by about half. Thus, the cost and time of production can be reduced as well. According to another aspect of the instant invention, by interposing a dome-shaped cup between the bottle and the milking portion, and by providing a non-return valve at the small hole interconnecting the milking portion and the suction portion, the milking apparatus may be retaining in a working mode for a longer period of time. Specifically, even if the mother's milk is atomized when drawn out, or if the milking apparatus is tipped or turned over, instances which could cause the small hole or other passages to become clogged up, such passages will remain open and the milking apparatus will continue to function properly.

Thus, one object of the instant invention is to reduce the number of components in the pressure adjusting mechanism D. To achieve the above object, the instant invention provides a milking apparatus comprising a bottle for storing drawn mother's milk, a milking section to be pressed against the mother's breast, and a suction portion including a suction or negative pressure generating section, for generating a suction or negative pressure in said bottle, and a pressure adjusting mechanism for adjusting the amount of suction, wherein, the above components are vertically connected together. The milking apparatus is characterized in that the pressure adjusting mechanism and the suction generating section are comprised of an attaching body formed with an open-air introducing hole, a compression coil spring, a valve rod having a tapered surface, a diaphragm having a valve seat adapted to closely contact with the tapered surface, a cap cooperating with said diaphragm to define a suction chamber therebetween, a pressure releasing push button having a cam surface and adapted to arrest the valve rod and a pressure adjusting knob for applying a pressing force to the cam surface of said push button.

Thus, in an apparatus according to the instant invention, as described above, the suction chamber between the diaphragm and the cap function as a pump to create a suction or negative pressure in bottle A. Further, by turning a pressure adjusting knob, the pressure releasing push button, having a cam surface thereon, is moved back and forth so that the valve rod arrested by the pressure releasing button is correspondingly separated from the valve seat of the diaphragm. If the pressure releasing push button is intermittently pressed, the valve rod is intermittently separated from the valve seat. As the valve rod is separated from the valve seat, the open air is introduced into the bottle so that the suction in the bottle is reduced.

It is another object of the instant invention to provide a suction portion C which is free from mother's milk at any time. To achieve this object, a milking apparatus is provided comprising, in combination and interconnected vertically, a bottle for collecting drawn out mother's milk, a milking portion adapted to be pressed onto the mother's breast, a suction portion which generates a suction within the bottle, and a dome-shaped cup with a collar interposed between the bottle and the milking portion with its vertex facing downward. The collar is provided with one or a plurality of suction holes for communication between the bottle and milking portion, and a through hole is formed in the vertex. In another aspect of this invention a milking apparatus is provided comprising, in combination interconnected vertically, a bottle for collecting drawn out mother's milk, a milking portion adapted to be pressed onto the mother's breast, a suction portion which generates a suction within the bottle and a dome-shaped cup with a collar which is interposed between the bottle and the milking portion with its. vertex facing downward. The collar being provided with one or a plurality of suction holes for communication between the bottle and milking portion, with a through hole formed in the vertex. Further, a non-return valve which is normally open is disposed at the communicating portion between the bottle and milking portion.

In the above described aspects of the instant invention, the interface between the bottle and milking portion is constricted by the dome-shaped cup, so that the drawn out mother's milk falls down along the inner surface of the cup to drip into the bottle. Also, if the milking apparatus is tipped or turned over, the mother's milk collected in the bottle will not flow into the suction portion because of the presence of the dome-shaped cup and non-return valve.

BRIEF DESCRIPTION OF THE DRAWINGS

The advantages of the instant invention will become apparent in the following description taken in conjunction with the drawings, wherein:

FIGS. 10 through 13 are assembled cross-sectional views of the pressure adjusting mechanism and the suction generating section in operation, wherein FIG. 10 is a view showing the state wherein a suction is being generated in the bottle, FIG. 11 is a view showing the state of air being exhausted, FIG. 12 is a view showing the state of the pressure adjusting knob being rotated to reduce suction and thus the milking force, and FIG. 13 is a view showing the state of the pressure releasing button being pressed to release the suction and thus remove the milking force;

FIGS. 17 through 22 all refer to the prior application, wherein FIG. 17 is a vertical cross-sectional side view of a pressure adjusting screw, FIG. 18 is a vertical cross-sectional side view of a pressure adjusting knob, FIG. 19 is a vertical cross-sectional side view of the pressure adjusting screw combined with the pressure adjusting knob, FIG. 20 is a right-hand side view of an attaching body, FIG. 21 is a right-hand side view of a diaphragm, and FIG. 22 is a left-hand side view of a cap;

DESCRIPTION OF THE PREFERRED EMBODIMENT

One embodiment of the invention will now be described with reference to Figs. 1 through 13.

Figure 1:
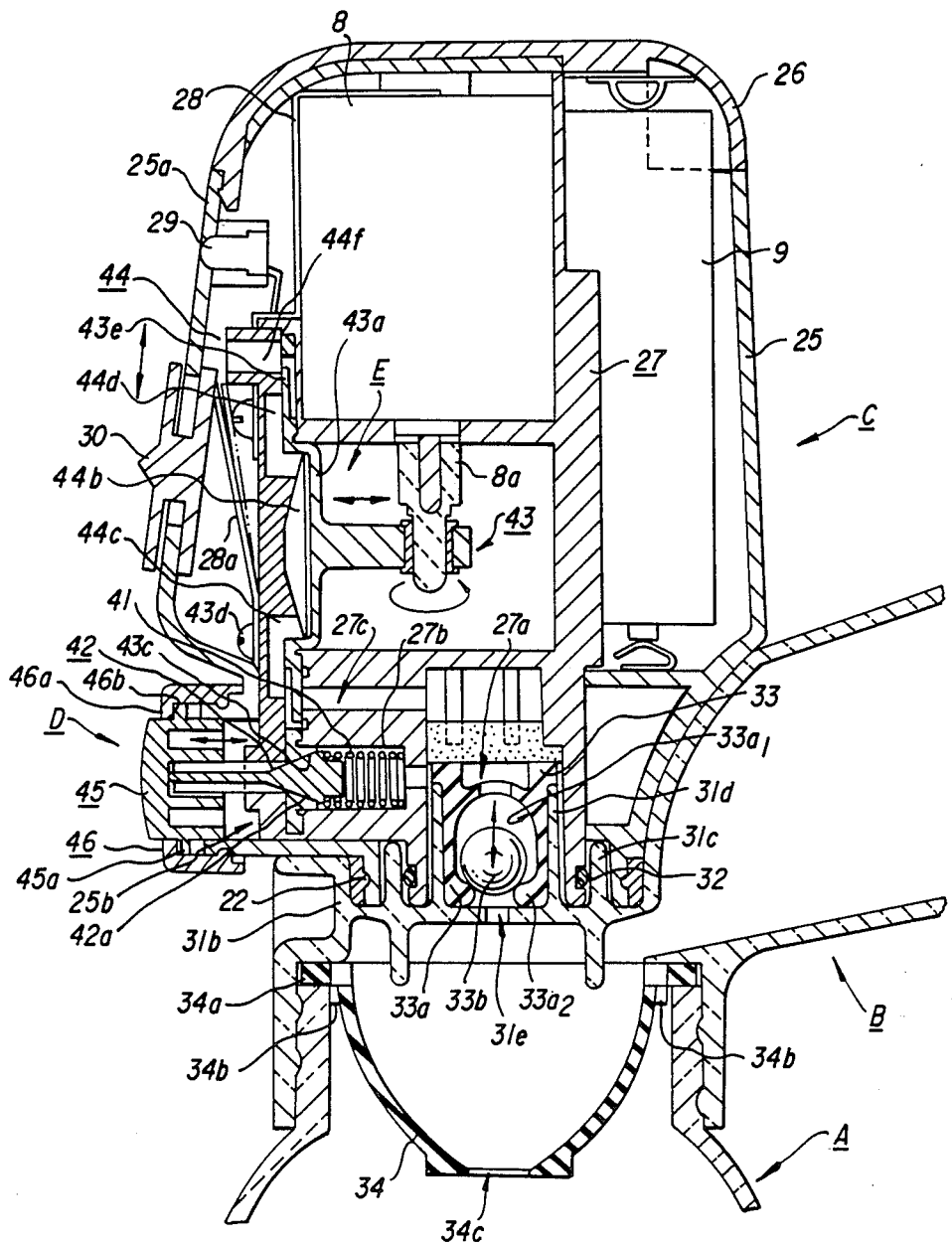
FIG. 1 is a vertical cross-sectional view of the main portions of the milking apparatus according to an embodiment of the instant invention.

FIG. 1 is a complete vertical cross-sectional view showing the upper portion of a bottle A, the base portion of a milking section B and a suction portion C.

The suction portion C comprises a main body 25, an upper lid 26 adapted to fit in the main body 25, and an attaching body 27 adapted to be positioned in the main body 25. The attaching body 27 has a motor 8 and a battery 9 which are electrically connected together by an elongated copper plate 28. However, the copper plate 28 is provided with a single movable contact 28a. The motor 8 has a crank pin 8a mounted thereon, while the battery 9 is replaceable by removing the upper lid 26 from the main body 25. The main body 25 is in the form of two cases 25a which are unconventionally vertically split and put together, with the upper and middle portions of one case being formed with notches. A light-emitting diode 29 is fitted in the upper notch to indicate the state of the charge of battery 9. A slide switch 30 is installed in the middle notch. Since switch 30 is installed in the notch of the case 25a, there is no need for screwing from inside as in the prior application. Below switch 30 and near the upper connecting portion 31b of milking section B, the main body 25 is formed with a horizontal hole 25b for receiving pressure adjusting mechanism D and a suction generating section E.

Figure 2:
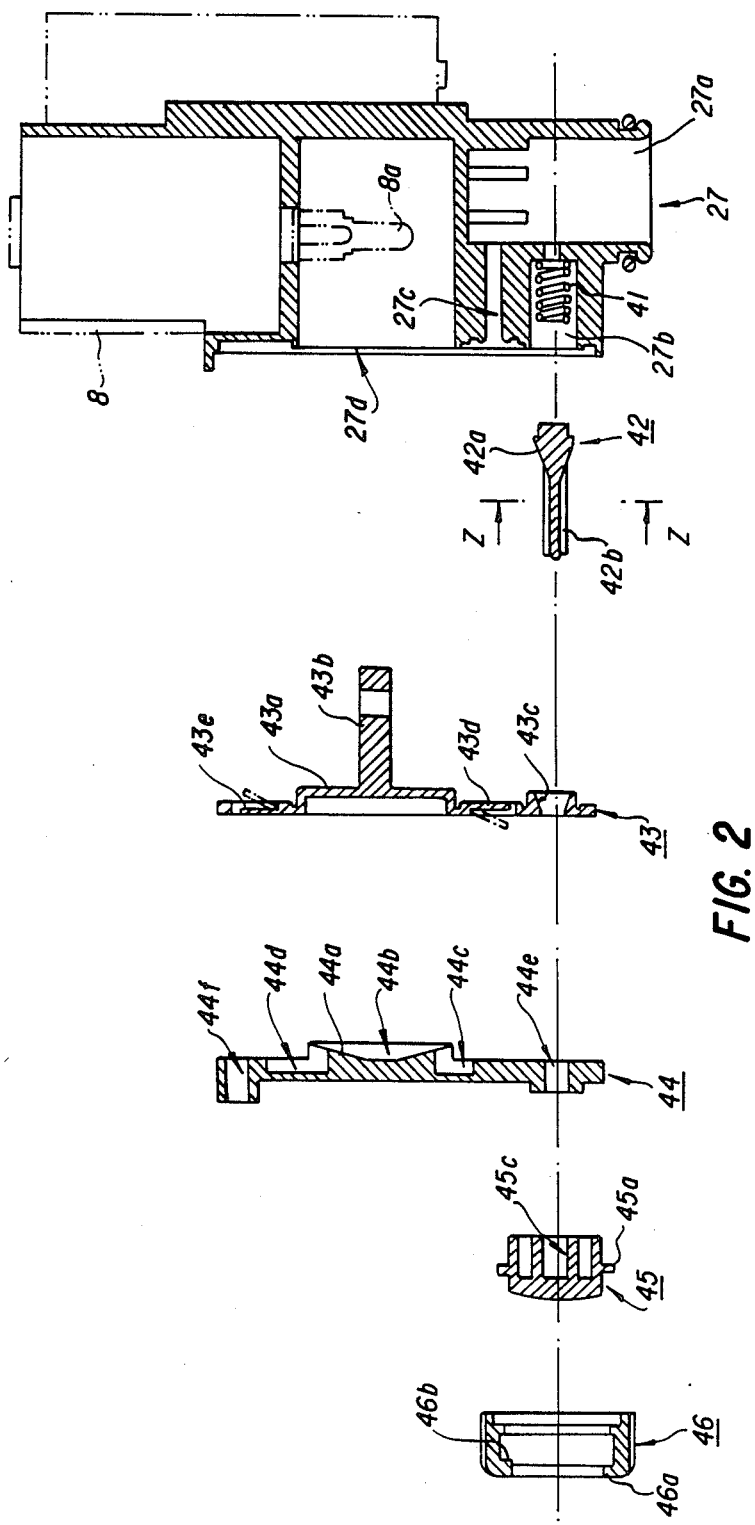
FIG. 2 is an exploded vertical cross-sectional front view of the pressure adjusting mechanism and the suction generating section of the apparatus of FIG. 1.

An exploded vertical cross-sectional view of the pressure adjusting mechanism D and the suction generating section E is shown in FIG. 2. In this figure, the right-hand side will hereinafter be referred to as the inner side and the left-hand side as the outer side. The pressure adjusting mechanism D and suction generating section have the following six parts installed on the outer side of the attaching body 27; a compression coil spring 41, a valve rod 42, a diaphragm 43, a cap 44, a pressure adjusting push button 45 and a pressure adjusting knob 46, in order from the inner to the outer side.

Figure 3:
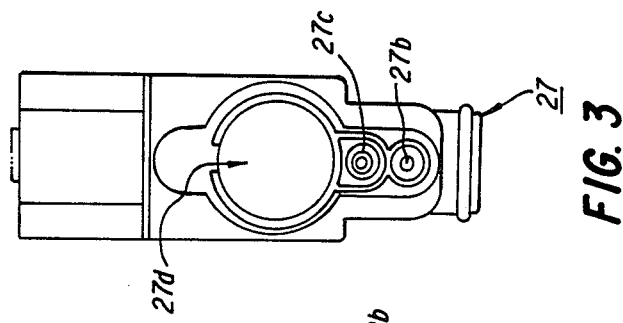
FIG. 3 is a left-hand side view of the attaching body of the apparatus of FIG. 1.

A left-hand side view of attaching body 27 is shown in FIG. 3, and will now be described with reference to this figure in combination with FIG. 2. The lower portion of attaching body 27 is formed with a vertical air suction hole 27a (See FIGS. 1 and 2). Further, the intermediate portion of the vertical hole 27a is formed with a stepped, outwardly directed open-air introducing hole 27b which is coaxial with the horizontal hole 25b. The upper portion of the open-air introducing hole 27b is formed with a suction hole 27c extending from the outer surface of the attaching body 27 to the air suction hole 27a. The intermediate portion of the attaching body 27 is formed with a fitting hole 27d whose lateral surface is circular.

The compression coil spring 41 is fitted in said open-air introducing hole 27b and bears against the stepped portion.

Figure 4:
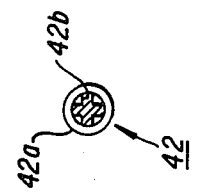
FIG. 4 is a vertical sectional view of the valve rod of the apparatus of FIG. 1.

Valve rod 42 has a conically expanding tapered surface 42a on its inner side portion and splines 42b of a crisscross cross-section on its outer side. A sectional view thereof taken along the line Z—Z is shown in FIG. 4.

Figure 5:
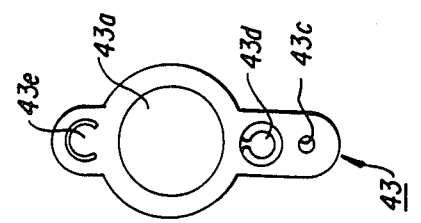
FIG. 5 is a left-hand side view of a diaphragm of the apparatus of FIG. 1.

A left-hand side view of diaphragm 43 is shown in FIG. 5 and will now be described with reference to this figure in combination with FIG. 2. The intermediate portion of the diaphragm 43 forms a circular vibrating portion 43a which projects inwardly, said projecting vibrating portion 43a being fitted in the fitting hole 27d of attaching body 27. A bushing portion 43d projects from the vibrating portion 43a toward motor 8 and is fitted on crank pin 8a of motor 8. Therefore, as motor 8 is rotated, the crank pin 8a is eccentrically rotated and the bushing portion 43b is moved back and forth, in order to vibrate vibrating portion 43a. The lower end of the diaphragm 43 forms a valve seat 43c coaxial with the horizontal hole 25b of the main body 25, said valve seat being closely contacted by the tapered surface 42a of valve rod 43 biased by compression coil spring 41. Diaphragm 43 is an elastic body, so that valve rod 42 is closely contacted with the valve seat portion 43b in the normal state without having to install a packing on the valve rod 52 as in the prior application. A suction valve 43d, which is a check valve which can be opened outwardly, is interposed between the vibrating portion 43a of diaphragm 43 and valve seat portion 43c. The upper portion of the vibrating portion 43a of diaphragm 43a is formed with a discharge valve 43e which is a check valve which can be opened inwardly.

Figure 6:
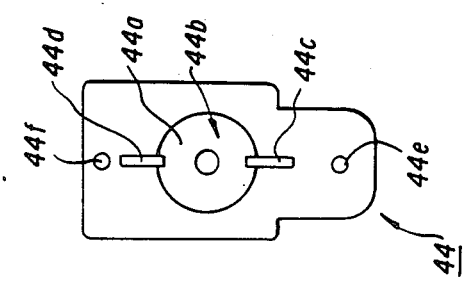
FIG. 6 is a right-hand side view of the cap of the apparatus of FIG. 1.

A right-hand side view of the cap 44 is shown in FIG. 6 and will now be described with reference to this figure in combination with FIG. 2. The middle inner portion of the cap 44 is formed with a projection 44a adapted to loosely fit in the vibrating portion 43a of diaphragm 43. The central portion of the diaphragm 43 is conically recessed to cooperate with the vibrating portion 43a of the diaphragm 43 to define a suction chamber 44b. A first narrow groove extends downwardly from suction chamber 44b and a second narrow groove 44d extends upwardly from suction chamber 44b. The lower side of the first narrow groove 44c is provided with an open-air introducing hole 44e coaxial with the horizontal hole 25b of the main body 25 in order to allow valve rod 42 to extend therethrough. The upper side of the second narrow groove 44d is provided with an exhaust hole 44f.

Figure 7:
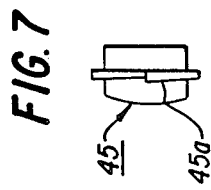
FIG. 7 is a top view of the pressure releasing push button of the apparatus of FIG. 1.
Figure 8:
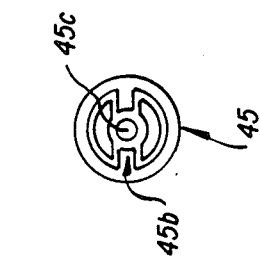
FIG. 8 is a right-hand side view of the pressure releasing push button of FIG. 7.

A plan view of the pressure release push button 45 is shown in FIG. 7 and a right-hand side view thereof is shown in FIG. 8, and will now be described with reference to these figures in combination with FIG. 2. The pressure releasing push button 45 is peripherally formed with a flange to serve as a cam surface as shown in FIG. 7. As shown in FIG. 8, a groove 45b is formed and this groove is engaged with pawls (not shown) projecting from both sides of the horizontal hole 25b so that the pressure release button 45 is allowed to move back and forth but not to rotate. Further, the middle portion is formed with a recess 45c having an abutment to arrest the movement of valve rod 42.

Figure 9:
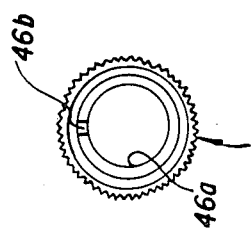
FIG. 9 is a right-hand side view of the pressure adjusting mechanism of the apparatus of FIG. 1.

A right-hand side view of the pressure adjusting knob 46 is shown in FIG. 9 and will now be described with reference to this figure in combination with FIG. 2. The pressure adjusting knob 46 is formed with a flange 46a around the outer end surface thereof to arrest the movement of pressure releasing push button 45 when the latter is urged outward. A projection 46a is formed on the inner side of the flange 46a at one place and is pressed against the cam surface 45a of the pressure releasing push button 45. When the pressure adjusting knob 46 is rotated, the projection 46b is also rotated to press the cam surface 45a of the pressure releasing push button 45. Thus, when the pressure adjusting knob 46 is rotated clockwise, the projection 46b is moved toward the inwardly recessed side of the cam surface 45a to move the pressure adjusting push button 45 outward, thereby urging the valve rod 42 outward.

The region where suction portion C and milking section B are fitted together will now be described with reference to FIG. 1.

The lower end of the main body 25 of the suction portion C which stores the pressure adjusting mechanism D is removably fitted in the upper connecting portion 31b of the milking section B. The upper connecting portion 31b is formed with outer and inner annular projections 31c and 31d, respectively, and a small hole 31e is formed in the middle of the inner annular projection 31d. The outer annular projection 31c is elastically contacted with an elastic body 32 fitted on the lower end of the main body 25. A check valve 33 is fitted in the inner annular projection 31d from above. The check valve 33 comprises a sleeve 33a made from synthetic resin, and a ball 33b fitted in the sleeve 33a. The upper surface of the sleeve 33a is internally formed with a concave surface $33a_1$ adapted to closely contact ball 33b and the lower end is formed with four ridges $33a_2$ so that the ball 33b is movable between the concaved surface $33a_1$ and $33a_2$. That is, in the normal state, the ball 33b is supported by ridges $33a_2$ to allow air to flow from the small hole 31e of the milking section B into the air suction hole 27a of attaching body 27. Further, if the milker topples over, ball 33b closely contacts the concave surface $33a_1$ so that the drawn milk stored in bottle A is prevented from flowing into the suction portion C. The milking section B is threadedly engaged at its lower connecting portion with the upper portion of the bottle A, and a dome-shaped cup 34 is installed between the upper end opening in the bottle A and the milking section B. The upper end opening in the cup 34 is formed with a flange 34a placed on the upper end opening in the bottle A. Flange 34a is formed with suction holes 34b at four places, for example, adapted to contact the lateral surface of the cup 34 so as to allow the passage of air from the bottle A. The lower diameter-reduced portion of cup 34 is formed with a through-hole 34c so that drawn out milk drips into bottle A. The reason for providing such dome-shaped cup 34 is to prevent the drawn out milk from flowing out in a short time when the milker topples over. If the cup 34 is made from rubber or soft plastic, the packing 23 which has heretofore been used in the prior application ca be dispensed with.

The operation of the milking apparatus according to the instant invention as set forth above, will be described specifically with reference to FIGS. 10 through 13. FIGS. 10 through 13 are assembled vertical cross-sectional front views of the pressure adjusting mechanism D and suction generation section E.

First, the operation of generating suction in bottle A will be described with reference to FIGS. 10 and 11. When switch 30 is turned on to rotate motor 8, crank pin 8a mounted on motor 8 is eccentrically rotated. Then, the vibrating portion 43a of diaphragm 43 is moved back and forth to continuously expand and contract the suction chamber 44b defined between diaphragm 43 and cap 44. As shown in FIG. 10, when the suction chamber 44b is expanded, the pressure in the suction chamber 44b is lowered. Then, air in the bottle flows successively through the through-hole 34c of cup 34, small hole 31e of milking section check valve 33, air suction hole 27a, and suction hole 27c, and suction valve 43d is opened to allow the air to flow through the first narrow groove 44c into suction chamber 44b. At this time, since discharge valve 43d is urged by the sucking force of the pressure in the direction to close the second narrow groove 44d, there is no possibility of the open air flowing through the discharge hole 44f into suction chamber 44b. In the normal state, the valve rod 42 is biased by compression coil spring 41 and since the tapered surface 42a of valve rod 42 is in close contact with valve seat 43c of diaphragm 43, there is no possibility of the open air flowing in through the open-air introducing hole 27b.

When the suction chamber 44b is contracted as shown in FIG. 11, discharge valve 43e is opened so that the air coming in from bottle A through the suction chamber 44b is discharged from the second narrow groove 44d through discharge hole 44f to the outside. At this time, since the suction valve 43d is not opened by pressure, the air flowing into suction chamber 44b will not flow out of suction hole 27c.

In this manner, the expansion and contraction of the suction chamber 44b, serving as a pump, causes the air in the bottle A to be sucked progressively into the suction chamber 44b and discharged through exhaust hole 44f. As a result, a suction is generated in the bottle so that the mother's breast closely contacting the cup portion 3 is sucked to have its milk drawn out.

Figure 12:
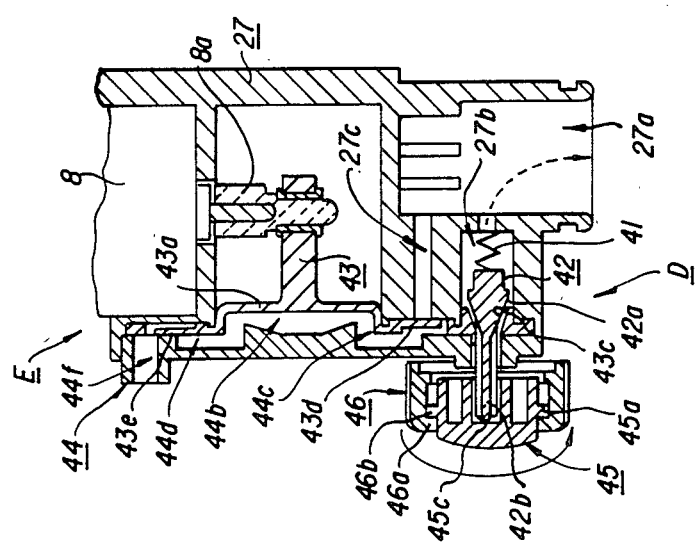
Figure 14:
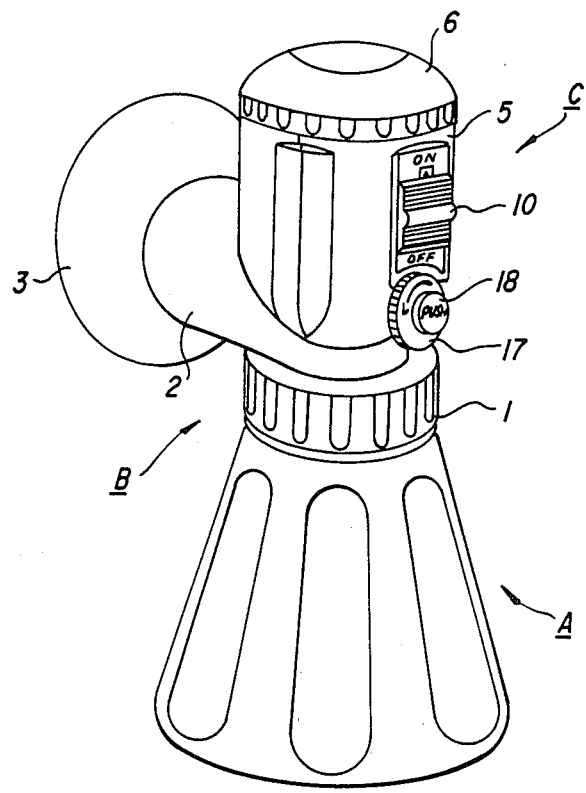
FIG. 14 is a perspective view of a milker according to a prior application.
Figure 15:
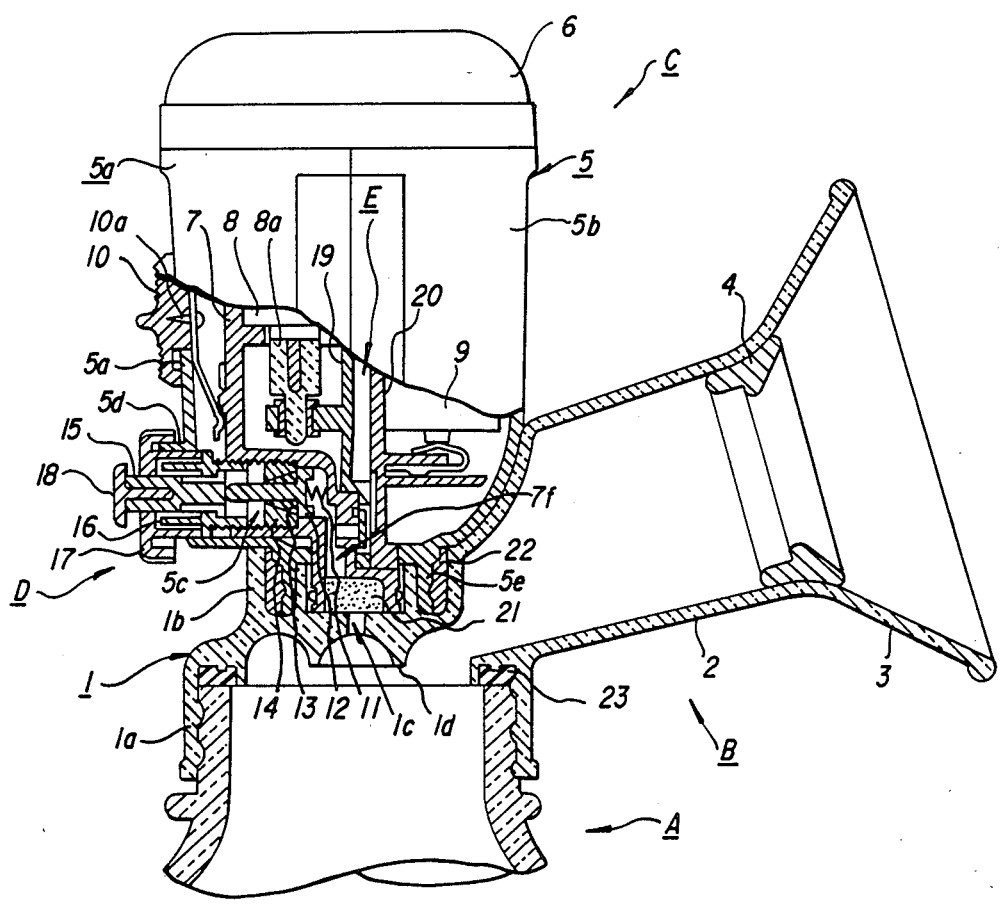
FIG. 15 is a fragmentary vertical cross-sectional view of the milker according to the prior application.
Figure 16:
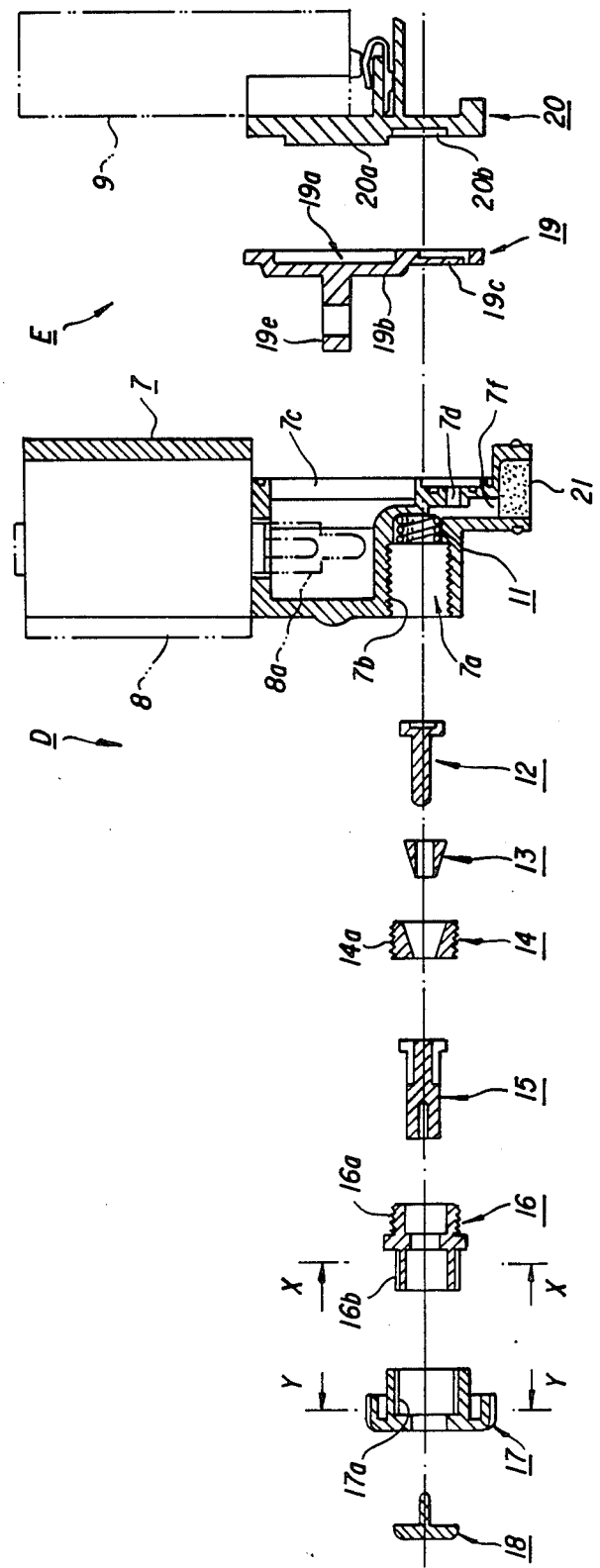
FIG. 16 is an exploded vertical cross-sectional front view of the pressure adjusting mechanism and suction generating section of the milker according to the prior application.
Figure 22:
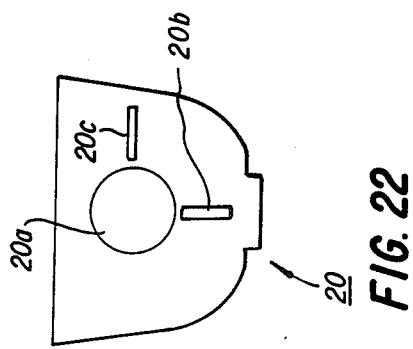
Figure 21:
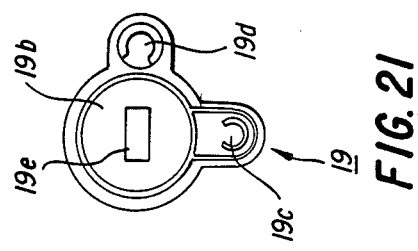
Figure 20:
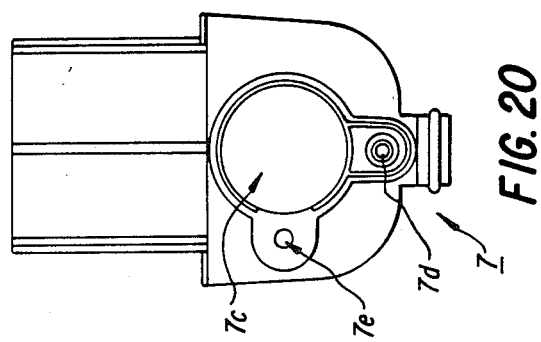
Figure 17:
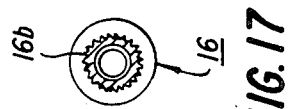
Figure 18:
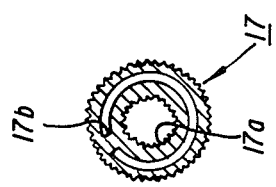
Figure 19:
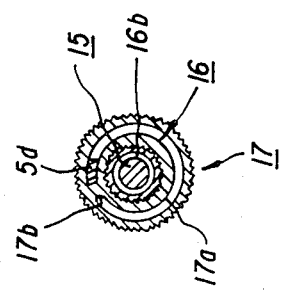

If the milking force is too high, it can be reduced by rotating the pressure adjusting knob 46 counterclockwise, as shown in FIG. 12. The projection 46b, which is provided on the inner side of pressure adjusting knob 46, presses the cam surface 45a of the pressure releasing push button 46. If the pressure adjusting knob 46 is rotated counterclockwise, the projection 46b presses the cam surface 45a exposed to the outer side. The pressure adjusting push button 45 will not rotate, nor will the pressure adjusting knob 46 move back and forth; therefore, the projection 46b presses the cam surface 45a, whereby valve rod 42 arrested by the recess 45c of the pressure releasing push button 45 is pressed inward against the compression force of the compression coil spring and the tapered surface 42a of valve rod 42 is separated from the valve seat 43c of diaphragm 43. Thereupon, open air flows from between the open air introducing hole 44e of cap 44 and the splines 42b and into the open air introducing hole 27b of attaching body 27. This means that air has been fed into the bottle A. Therefore, when diaphragm 43 is operated to draw the air from the bottle A, the open air flows in through the open air introducing holes 44e and 27b; therefore, the air suction pressure in the bottle decreases and so does the milking force. That is milking can be effected with a continuously low milking force.

Figure 13:
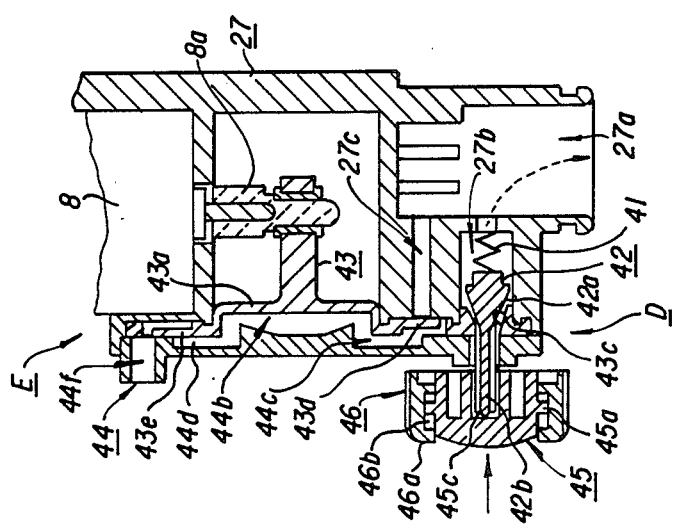

Instead of using a continuously low milking force, the milking force may be intermittently varied. In that case, as shown in FIG. 13, the pressure adjusting push button 45 is pressed. Thereupon, the valve rod 42 arrested by the abutment of recess 45c of the pressure releasing push button 45 is moved inward against the compression force of the compression coil spring 41. Thus, the tapered surface 42a of valve rod 42 is moved wide apart from valve seat 43c of diaphragm 43, causing the open air to gush through the open air introducing holes 44e and 27b into the air suction hole 27a of attaching body 27. Thus, the suction pressure in the bottle A instantaneously disappears and so does the milking force. When the pressing force on the pressure releasing button 45 is removed, the compression force of compression coil spring 41 biases the valve rod 42 outward and the tapered surface 42a of the valve rod 42 is brought again into close contact with valve seat 43c. Thus, the suction pressure in the bottle A again increases. Therefore, by intermittent pressing operation on the pressure releasing such button 45 to thereby intermittently vary the suction pressure in bottle A, the mother's nipple can receive a suitable degree of stimulus for milking similar to the suckling action of a baby.

All the operations described so far can be performed by one hand because of the installation of the pressure releasing push button 45 and the pressure adjusting knob 46 on the lower lateral surface of the suction portion C, while allowing the mother's other hand to be free to massage the area around her breast or to help in milking.

The non-return check valve and the dome-shaped cup will be described in more detail with reference to FIGS. 23–29. In these figures barrel 2, cup portion 3, adaptor 4, main body 5, and upper lid 6 retain the reference numerals as described above. The remaining parts have different reference numerals from those set forth above.

Figure 23:
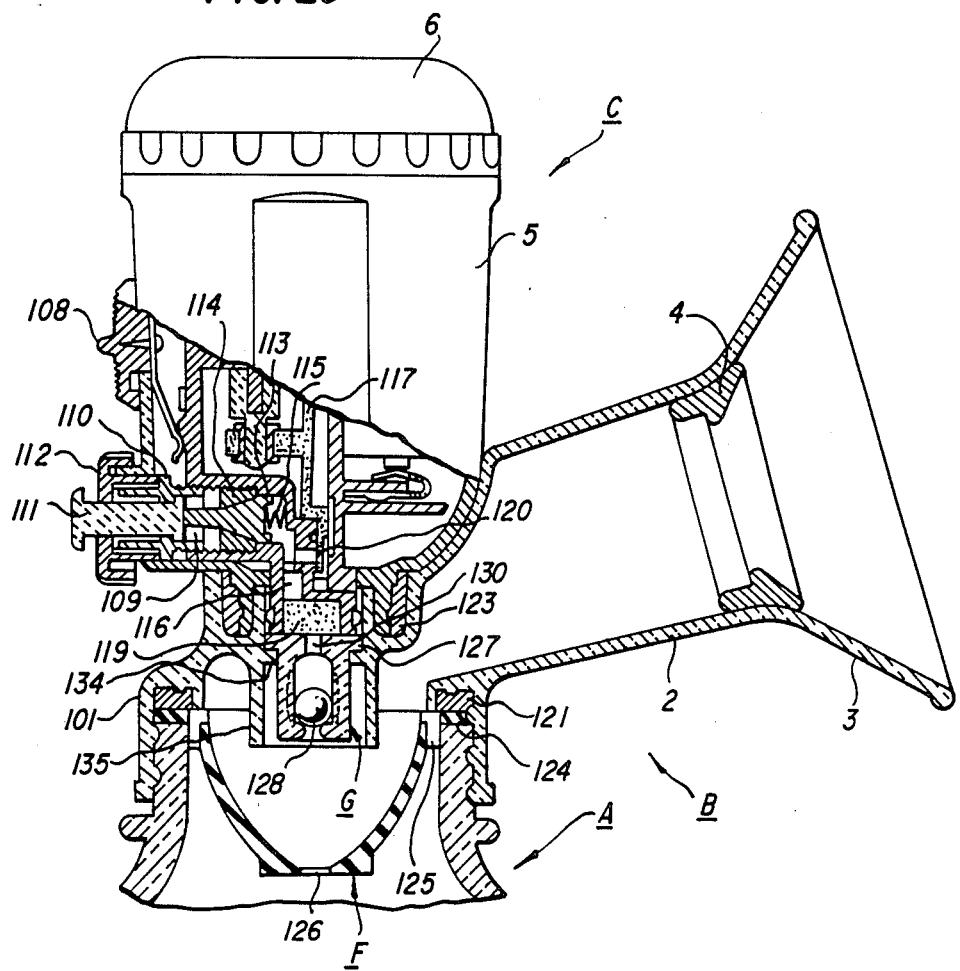
FIG. 23 is a partially cutaway cross-sectional view of another embodiment of the instant invention.

The device of FIG. 23 is similar to the device of FIG. 1, with a slightly different structure of the non-return check valve G and its surrounding structure.

Figure 24:
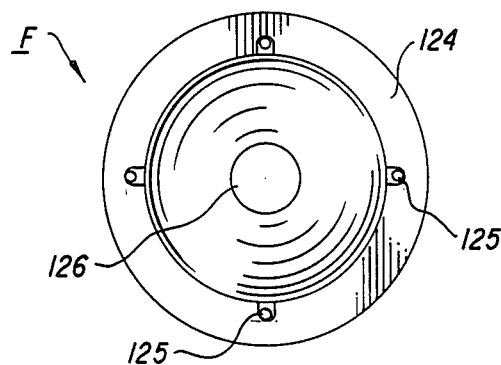
FIG. 24 is a plan view of the cup of FIG. 23.
Figure 25:
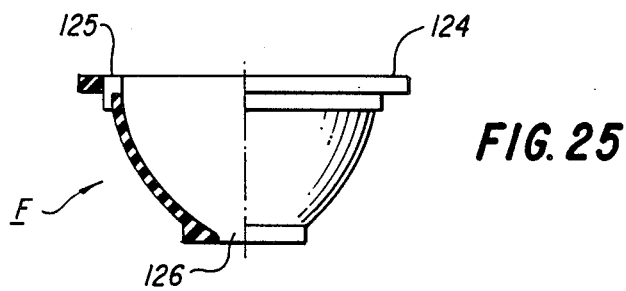
FIG. 25 is a front view of the cup of FIG. 23, with the left half in cross-section.
Figure 26:
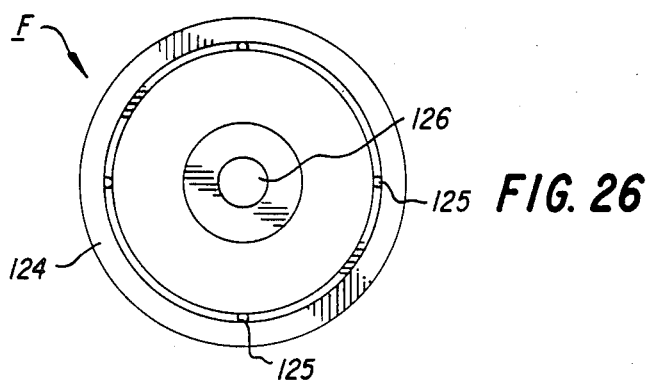
FIG. 26 is a bottom view of the cup of FIG. 23.
Figure 27:
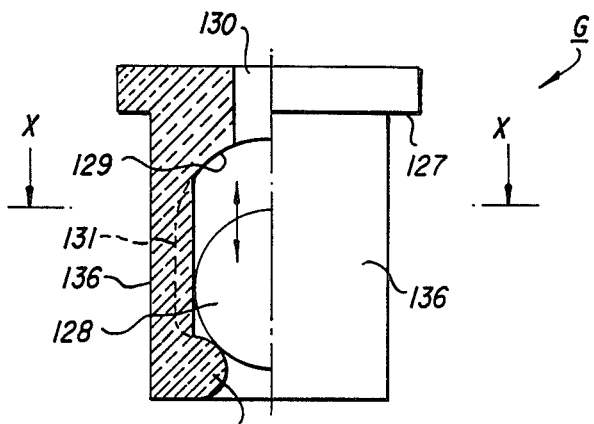
FIG. 27 is a front view of the non-return valve of FIG. 23, with the left half in cross-section.
Figure 28:
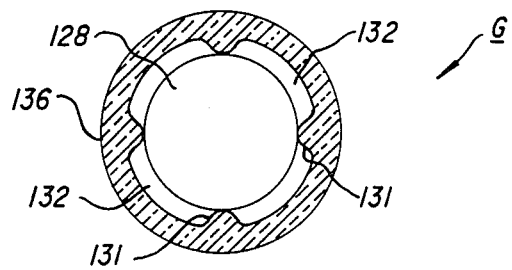
FIG. 28 is a cross sectional view taken along the line X—X of FIG. 5.
Figure 29:
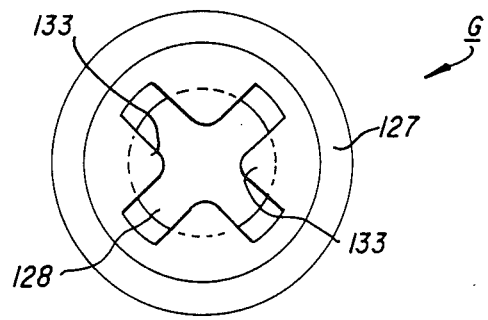
FIG. 29 is a bottom view of the non-return valve of FIG. 23.

Specifically, in FIG. 23, F indicates a dome-shaped cup, whose plan view, a left half cross-sectional front view and a bottom view are respectively shown in FIG. 24, FIG. 25, and FIG. 26. Cup F is provided with collar 124 around the upper end opening which is interposed between the upper end-opening of bottle A and packing 121. However, if a material of the cup F is replaced with rubber or a soft plastic or the like, collar 124 of the cup F may be used commonly in place of packing 121. In the collar 124, suction holes 125 are formed, for example, at four placed to adjoin the side of the cup F, and a through hole 126 is formed in the vertex of the cup F. Insides of the bottle A and cup are in communication with each other by virtue of the suction holes 125 and the through hole 126. Through the upper end opening of bottle is constricted by the cup F. air in the bottle is always drawn int the suction portion A through the holes 125 and 126 and the inside of bottle A is kept with a negative pressure or suction, so that the mother's milk is constantly drawn out and drips into the bottle A.

The reference G denotes a generally cylindrical non-return valve made of an elastic material, provided with a collar 127 around its upper end and retaining a ball 128 made of, for example, metal, for upward and downward movement. A left half sectional front view, a sectional view taken along the line X—X of the FIG. 27, and a bottom view are respectively shown in FIG. 27, FIG. 28, and FIG. 29. The non-return valve G comprises a cylindrical body 136 made of, for example, a plastic material and ball 128 inserted into the body 136 having a concave surface 129 formed on the upper surface of its hollow portion for close contact with ball 128 and a passage hole 130 extending therethrough at the center. On the inner wall of the hollow portion of cylindrical body 136, for example, four projection rails 131 extend from concave surface 129 to the lower end so that ball 128 can be moved up and down smoothly. Gaps 132 are formed between ball 128 and the inner wall to allow the air in bottle A to be draw therethrough. At the lower end of the hollow portion of cylindrical body 136, tips 133 of projection rails 131 protrude inwardly toward the center to support ball 128.

Around the hole in the base 101 of the milking portion B, which corresponds to but is larger than the small hole in the milking portion of the conventional milking apparatus, a flange 134 is arranged to engage with the upper end collar 127 of the non-return valve G. Around the base 101 of the milking portion B, there is also provided an outer ring 135 surrounding the non-return valve G in a spaced apart relationship to prevent an atomized mother's milk from adhering directly to the non-return valve G.

The operation of the milking apparatus, as set forth above with respect to FIGS. 23–29, will now be described.

When switch 112 is turned on, diaphragm 117 starts to vibrate. Although the ball 128 is positioned in the non-return valve G, gaps 132 are formed between the projection rails 131, and thus air in bottle A is drawn into the air suction port 116 in the suction portion C from through hole 126 in the cup F through gaps 132 in the non-return valve G, therefore generating a suction in bottle A. Ball 138 in the non-return valve G is made of metal and is heavy, so that it will never reach passage hole 130 because of the movement of air around it. Even if the mother's milk is extracted in an atomized state due to a strong milking force, since the cup F is of an inverted dome-shape, the atomized milk is deposited on its inner surface and condenses to form drops, which drip into bottle A through hole 126 in the cup Also, when the mother's milk is extracted and collected in the cup F, in such a large quantity as to clog hole 126, air in bottle A is also drawn through the suction ports 125 provided in collar 124, and thus bottle A retains a negative pressure and milking can continue.

Even when the milking apparatus is tipped or turned over, since the upper end opening of bottle A is constricted by the cup F, the mother's milk in bottle is intercepted by the curved portion of cup F and is prevented from flowing out into the milking portion B. Although suction holes 125 are provided in collar 124, since the diameter of suction holes 125 is smaller, the mother's milk in the bottle A will not flow into the cup F at a breath, thus preventing the mother's milk from flowing into the suction portion C so long as the apparatus is not kept in that tipped over state for a long period of time. Even if the milk in bottle A has flowed into cup F in a large quantity from the through hole 126, since the non-return valve G is provided on the base 101 of milking portion B and the ball 128 clogs the open and close hole 130 by the lateral turning or tipping of the milking apparatus, and the mother's milk will not flow into the suction portion C.

Although specific embodiments of the instant invention have been described above and illustrated in the accompanying drawings in order to be more clearly understood, the above description is made by way of example and not as a limitation to the scope of the instant invention. It is contemplated that various modifications apparent to on of ordinary skill in the art could be made without departing from the scope of the invention which is to be determined by the following claims

I claim:

1. A milking apparatus, comprising:
    a bottle for storing drawn out mother's milk;
    a milking section to be pressed against the mother's breast; and
    a suction portion connected vertically with said milking section and said bottle, respectively, including a suction generating section for generating a suction in said bottle, and a pressure adjusting mechanism for adjusting the amount of suction in said bottle;
    wherein said suction generating section and said pressure adjusting mechanism include, (a) an attaching body having an open-air introducing hole in communication with said bottle (b) a compression coil spring bearing against said attaching body (c) a valve rod having a tapered surface, said valve rod bearing against said coil spring and being biased away from said attaching body by said coil spring, (d) a diaphragm having a valve seat for closely contacting, said tapered surface of said valve rod (e) a cap cooperating with said diaphragm to define a suction chamber therebetween (f) a pressure releasing push button having an abutment to bear against said valve rod to balance the biasing force of said spring, and a cam surface, and (g) a pressure adjusting knob for applying a pressing force to said cam surface to move said pressure releasing push button and valve rod against the biasing force of said spring.

2. The apparatus of claim 1, wherein said cam surface of said pressure releasing push button is an annular surface around the outer periphery of said push button, said cam surface varying in the axial direction of said push button.

3. The apparatus of claim 2, wherein said pressure releasing push button is only movable in the axial direction thereof, and said pressure adjusting knob is only movable in a rotational direction.

4. The apparatus of claim 3, wherein said pressure adjusting knob surrounds said cam surface of said push button, and said pressure adjusting knob has an inwardly extending projection bearing against said cam surface, such that the rotational movement of said pressure adjusting knob causes the axial movement of said push button against said biasing spring.

5. A milking apparatus, comprising:
a bottle for storing drawn out mother's milk;
a milking section to be pressed against the mother's breast;
a suction portion, connected vertically with said milking section and said bottle, respectively, for generating a suction in said bottle; and
a dome-shaped cup interposed between said bottle and milking portion with a vertex thereof facing into said bottle, said cup having a through hole formed on the vertex thereof.

6. The milking apparatus of claim 5, wherein said dome-shaped cup has a collar with at least one suction hole communicating between said bottle and said milking portion.

7. The milking apparatus of claim 6, wherein said dome-shaped cup has a plurality of suction holes.

8. The milking apparatus of claim 5, wherein said dome-shaped cup is made of an elastic material.

9. The apparatus of claim 5, further comprising a non-return valve, maintained in a normally open state and positioned at a small hole communicating air between said milking section and said suction portion, such that said non-return valve becomes closed when said milking apparatus is turned laterally, to prevent milk from entering said suction portion 10. The milking apparatus of claim 9, wherein said non-return valve is a check valve, comprising:
a cylindrical body having an opening at each end thereof and an elongated cavity therein;
a heavy ball disposed in said cavity and movable between said openings,
axially extending ridges formed in said cavity and supporting said ball therebetween, such that air flows around said ball except when said ball is forced to one of said two ends to become closed.

* * * * *

UNITED STATES PATENT AND TRADEMARK OFFICE
CERTIFICATE OF CORRECTION

PATENT NO.   :   4,886,494
DATED        :   December 12, 1989
INVENTOR(S)  :   Yasuo MORIFUJI It is certified that error appears in the above-identified patent and that said Letters Patent is hereby corrected as shown below:

On the cover page, after Item [76], insert:

--[73] Assignee: JEX Company Limited, Osaka, Japan--

Signed and Sealed this

Fifth Day of March, 1991

*Attest:*

HARRY F. MANBECK, JR.

*Attesting Officer*        *Commissioner of Patents and Trademarks*